US011318208B2

(12) United States Patent
Becker et al.

(10) Patent No.: US 11,318,208 B2
(45) Date of Patent: May 3, 2022

(54) SYNTHETIC COMPOUND

(71) Applicant: Syntab Therapeutics GmbH, Würselen (DE)

(72) Inventors: Christian Becker, Klosterneuberg (AT); Manuel Brehs, Delbrück (DE); Karine Thewes, Vienna (AT); Ute Steinbusch, Alsdorf (DE); Andre J G Pötgens, Simpelveld (NL); Janett Schwarz, Aachen (DE)

(73) Assignee: SYNTAB THERAPEUTICS GMBH, Würselen (DE)

(*) Notice: Subject to any disclaimer, the term of this patent is extended or adjusted under 35 U.S.C. 154(b) by 0 days.

(21) Appl. No.: 16/304,121

(22) PCT Filed: May 24, 2017

(86) PCT No.: PCT/EP2017/062576
§ 371 (c)(1),
(2) Date: Nov. 21, 2018

(87) PCT Pub. No.: WO2017/202933
PCT Pub. Date: Nov. 30, 2017

(65) Prior Publication Data
US 2019/0201539 A1  Jul. 4, 2019

(30) Foreign Application Priority Data
May 24, 2016  (GB) .................................... 1609083

(51) Int. Cl.
*A61K 47/64* (2017.01)
*C07K 16/28* (2006.01)
*C07K 14/705* (2006.01)
*A61K 39/39* (2006.01)
*C07K 7/06* (2006.01)
*C07K 5/103* (2006.01)
*A61K 47/68* (2017.01)
*A61K 47/60* (2017.01)
*A61K 38/08* (2019.01)

(52) U.S. Cl.
CPC .............. *A61K 47/64* (2017.08); *A61K 38/08* (2013.01); *A61K 39/39* (2013.01); *A61K 47/60* (2017.08); *A61K 47/6811* (2017.08); *A61K 47/6849* (2017.08); *C07K 5/1013* (2013.01); *C07K 7/06* (2013.01); *C07K 14/705* (2013.01); *C07K 16/2842* (2013.01)

(58) Field of Classification Search
CPC ........ A61K 38/08; A61K 39/39; A61K 47/60; A61K 47/64; A61K 47/6811; A61K 47/6849; A61P 25/00; A61P 31/04; A61P 31/12; A61P 35/00; A61P 37/06; A61P 3/00; C07K 14/705; C07K 16/2842; C07K 5/1013; C07K 7/06
See application file for complete search history.

(56) References Cited

U.S. PATENT DOCUMENTS

| 4,064,118 A | 12/1977 | Wong |
| 4,522,752 A | 6/1985 | Sisto et al. |
| 5,328,899 A | 7/1994 | Boublik |
| 8,470,963 B2 | 6/2013 | Koltermann |

FOREIGN PATENT DOCUMENTS

| EP | 1398322 A1 | 3/2004 |
| EP | 1398327 A1 | 3/2004 |
| EP | 1398328 A1 | 3/2004 |
| EP | 2573569 A1 | 3/2013 |
| JP | 2009-541398 A | 11/2009 |
| WO | 1996/040749 A1 | 12/1996 |
| WO | 1996/040772 A2 | 12/1996 |
| WO | 2001/038342 A2 | 5/2001 |
| WO | 2001/040275 A2 | 6/2001 |
| WO | 2001/091780 A1 | 12/2001 |
| WO | 2002/055543 A2 | 7/2002 |
| WO | 2004/024761 A1 | 3/2004 |
| WO | 2004/100997 A2 | 11/2004 |
| WO | 2004/101600 A2 | 11/2004 |
| WO | 2004/101606 A2 | 11/2004 |
| WO | 2004/101611 A2 | 11/2004 |
| WO | 2008/000517 A1 | 1/2008 |
| WO | 2010/089019 A1 | 8/2010 |

OTHER PUBLICATIONS

Southgate et al. Identification of Formyl Peptides from Listeria monocytogenes and Staphylococcus aureus as Potent Chemoattractants for Mouse Neutrophils. The Journal of Immunology, 2008, vol. 181, pp. 1429-1437. (Year: 2008).*
He et al. Structural Determinants for the Interaction of Formyl Peptide Receptor 2 with Peptide Ligands. JBC, 2014, vol. 289, No. 4, pp. 2295-2306. (Year: 2014).*
Fishburn, C. Simone, Bacteria's painful truth. SciBX: Science-Business exchange. Nature Publishing Group. 2013; 6 (36): 4-5.
Miyazaki, M. et al., Dimeric Chemotactic Peptides Discriminate Between Chemotaxis and Superoxide Production of Human Neutrophils. J Biochem. 1995; 117(3):489-94.
Schoenafinger, G. et al., Formylation Domain: An Essential Modifying Enzyme for the Nonribosomal Biosynthesis of Linear Gramicidin. J Am Chem Soc. 2006; 128(23):7406-7.
Seki, T. et al., Mitocryptide-2, a Neurophil-Activating Cryptide, is a Specific Endogenous Agonist for Formyl-Peptide Receptor-like 1. Biochem Biophys Res Commun. 2011; 404(1):482-7.

(Continued)

Primary Examiner — Marcela M Cordero Garcia
(74) Attorney, Agent, or Firm — Ballard Spahr LLP

(57) ABSTRACT

The present invention relates to a synthetic compound comprising at least one effector moiety and at least one binder moiety, wherein the effector moiety is associated to the binder moiety, and wherein further the effector moiety comprises a N-formyl methionine peptide which comprises an isoleucine residue (FIG. 1).

10 Claims, 16 Drawing Sheets
Specification includes a Sequence Listing.

(56) References Cited

OTHER PUBLICATIONS

International Search Report and Written Opinion dated Aug. 22, 2017 by the International Searching Authority for Patent Application No. PCT/EP2017/062576, which was filed on May 24, 2017 and published as WO 2017/202933 on Nov. 30, 2017 (Inventor—Becker et al.; Applicant—Ayntab Therapeutics GmbH) (11 pages).
Gobbo, M. et al., Synthesis and Biological Activities of Head-to-Tail Cyclic Bradykinin Analogues of Varying Ring Size. Int J Peptide Prot Res. 1997; 50(5):336-41.
Ishida, I., Peptides that Contain Unnatural Amino Acids: Toward Artificial Proteins. Rev Heteroatom Chem. 1999; 19:79-142 (Abstract only—6 pages).
James, G.L. et al., Benzodiazepine Peptidomimetics: Potent Inhibitors of Ras farnesylation in Animal Cells. Science. 1993; 260(5116):1937-42.
Kim, C. et al., The Hemopoietic Rho/Rac Guanine Nucleotide Exchange Factor Vavl Regulates N-Formyl-Methionyl-Leucyl-Phenylalanine-Activated Neutrophil Functions. J Immunol. 2003; 171(8):4425-30.
Koppitz, M. et al., Synthesis of Unnatural Lipohilic N-(9H-Fluoren-9-ylmethoxy)carbonyl-Substituted α-Amino Acids and Their Incorporation into Cyclic RGD-Peptides: A Structure-Activity Study. Helv Chim Acta. 1997; 80(4):1280-300.
O'Donnell, M.J. et al., Solid-Phase Unnatural Peptide Synthesis (UPS). J Am Chem Soc. 1996; 118(25):6070-1.
O'Donnell, M.J. et al., Solid-Phase Synthesis of Unnatural Amino Acids Using Unactivated Alkyl Halides. Tetrahedron Lett. 1997; 38(41):7163-6.
Scott, W.L. et al., The Solid Phase Synthesis of α,α-Disubstituted Unnatural Amino Acids and Peptides (di-UPS). Tetrahedron Lett. 1997; 38:3695-8.
Tam, J.P. and Lu, L.-A., A Biomimetic Strategy in the Synthesis and Fragmentation of Cyclic Protein. Protein Sci. 1998; 7(7):1583-92.
Zhang, L. and Tam, J.P., Synthesis and Application of Unprotected Cyclic Peptides as Building Blocks for Peptide Dendrimers. J Am Chem Soc. 1997; 119(10):2363-70.
Obrist, R. et al., Chemotactic Monoclonal Antibody Conjugates: A Comparison of Four Different f—MET—Peptide—Conjugate. Biochem Biophys Res Commun. 1988; 155(3):1139-44.
Obrist, R. et al., Monocyte Chemotaxis Mediated by Formyl-Methionyl-Leucyl-Phenylalanine Conjugated with Monoclonal Antibodies Against Human Ovarian Carcinoma. Int J Immunopharmacol. 1983;5(4):307-14.
Obrist, R. et al., Enhancement of macrophage invasion of tumors by administration of chemotactic factor-antitumor antibody conjugates. Cellular Immunology, vol. 81, No. 1, Oct. 1, 1993; pp. 169-174.
Office Action was dated Feb. 26, 2021 by the European Patent Office for EP Application No. 17 728 085.6, filed on Jan. 2, 2019 and published on Apr. 10, 2019 (Applicant—Syntab Therapeutics GmbH) (6 Pages).
He, Hui-Qiong, et al. Structural determinants for the interaction of formyl peptide receptor 2 with peptide ligands. J Biol Chem., 2014, vol. 289, No. 4, p. 2295-2306.
Rot, A, et al. A series of six ligands for the human formyl peptide receptor: tetrapeptides with high chemotactic potency and efficacy. Proceedings of the National Academy of Sciences of the United States of America, 1987, vol. 84, p. 7967-7971.
Southgate, E.L., et al. Identification of formyl peptides from Listeria monocytogenes and *Staphyloccus aureus* as potent chemoattractants for mouse neurtrophils, J. Immunol., 2008, vol. 181, No. 2, p. 1429-1437.
Office Action was dated Apr. 19, 2021 by the Japanese Patent Office for JP Application No. 2019-514855, filed on Nov. 22, 2018 (Applicant—Syntab Therapeutics GmbH) (4 Pages).

* cited by examiner

A

B

| Seq ID No | Sequence | Three letter code | | Target |
|---|---|---|---|---|
| Binder peptides/peptidomimetics | | | | |
| 1 | cdGY(3-NO2)GHypNc | Xa1Xa2GlyXa3GlyXa4AsnXa1 | Xa1 = D-Cystein; Xa2 = D-Aspartat; Xa3 = Nitrotyrosine; Xa4 = 4-Hydroxiproline | α3 Integrin |
| 2 | RGDLATLRQL | ArgGlyAspLeuAlaThrLeuArgGlnLeu | | α$_v$β6 Integrin (β-Kette) |
| Effector peptides/peptidomimetics | | | | |
| 3 | fMIFL | fMetIlePheLeu | fMet = formylated Methionine | formyl peptide receptors |
| 4 | fMLFII | fMetLeuPheIleIle | fMet = formylated Methionine | formyl peptide receptors |
| 5 | fMIVTLF | fMetIleValThrLeuPhe | fMet = formylated Methionine | formyl peptide receptors |
| 6 | fMLFIIK | fMetLeuPheIleIleLys | fMet = formylated Methionine | formyl peptide receptors |
| 7 | fMIFTLF | fMetIlePheThrLeuPhe | fMet = formylated Methionine | formyl peptide receptors |

Fig. 15

SYNTHETIC COMPOUND

CROSS-REFERENCE TO RELATED PATENT APPLICATIONS

This application is a U.S. national phase application of International Application No. PCT/EP2017/062576, which was filed May 24, 2017, and which claims the benefit of priority to Great Britain Application No. 1609083.9, filed on May 24, 2016. The content of these earlier filed applications is hereby incorporated herein by reference.

SEQUENCE LISTING

The Sequence Listing submitted herewith as a text filed named "13318_0038U1_Sequence_Listing.txt," created on Apr. 7, 2020, and having a size of 4,096 bytes is hereby incorporated by reference pursuant to 37 C.F.R. § 1.52(e)(5).

The present invention is related to novel synthetic compounds which are useful, among others, for the treatment of diseases.

In the international application WO200800517 synthetic compounds are disclosed that comprise one or more effector moieties and one or more binder moieties, linked to one another. The effector moieties are ligands to at least one pathogen pattern recognition receptor (PRR) and the binder moieties bind to a marker of a tumor cell. Preferably, the effector moieties are ligands to a formyl peptide receptor, preferably N-formyl methionine peptides, like fMLF (N-formyl Met-Leu-Phe) or fMMYALF (N-formyl-Met-Met-Tyr-Ala-Leu-Phe; SEQ ID NO: 8)).

The international application WO201089019 discloses further N-formyl methionine peptides that can be used in this concept, namely fML (N-formyl-Met-Leu); fMLP (N-formyl-Met-Leu-Pro), fMLKK (N-formyl-Met-Leu-Lys-Lys; SEQ ID NO: 9)); fMLPKK (N-formyl-Met-Leu-Pro-Lys-Lys; SEQ ID NO: 10)) and fMLFKK (N-formyl-Met-Leu-Phe-Lys-Lys; SEQ ID NO: 11).

These peptides bind, in vivo, to the formyl peptide receptor (FPR), and serve as potent immunological homing signals for sites of bacterial infection, signaling several phases of neutrophil response and activation, that can including chemoattraction, stimulation of production and release of immunosignaling molecules (e.g., interleukins, cytokines, etc.), as well as degranulation, a cellular process that includes the production and release of both chemical (e.g., hydrogen peroxide and other reactive oxygen radical species) and enzymatic agents (e.g., elastase and other digestive enzymes) capable of mediating destruction of the foreign agent or pathogen.

The cellular response mediated by the formyl peptide receptor can include cellular polarization and transmigration, generation of superoxide $O_2$ radicals through respiratory burst oxidase, degranulation and release of a variety of various degradative enzymes, as well as phagocytosis.

These molecules have thus been suggested to act as effectors in a synthetic compound concept, where they are linked to binding moieties that are specific for a given target structure. The constructs thus achieved detect target structures, e.g., malignancy markers on a tumor cell, and activate the immune system in a target-specific manner in order to attack, or inactivate, the target structures, or the cells bearing them.

The term "effector" or "effector moiety" preferably refers to any molecular structure, which induces, controls or otherwise is part of an immunological response, of either the acquired/adaptive or the innate immune system. Effector molecules are capable of binding to a receptor, though not necessarily at the binding site of the natural ligand. Effectors can modulate signal transduction when used alone, i.e., can be surrogate ligands, or can alter signal transduction in the presence of the natural ligand.

The synthetic compounds disclosed in WO200800517 and WO201089019 can thus act according to a similar principle as the well-known IgG-based antibodies, which have a binding moiety (the variable region, or the CDRs comprised therein), and an effector moiety (the Fc region).

SUMMARY OF THE PRESENT INVENTION

It is one object of the present invention to provide novel synthetic compounds that allow an improved target specific activation of a patient's immune system.

It is one further object of the present invention to provide novel synthetic compounds which open up new possibilities of the treatment of diseases.

It is one other object of the present invention to provide novel synthetic compounds which allow an improvement in the treatment of Neoplastic diseases, Autoimmune diseases, Neuropathological diseases, Metabolic diseases and/or Infectious diseases.

These and other objects are solved by the subject matter of the present invention.

EMBODIMENTS OF THE INVENTION

Before the invention is described in detail, it is to be understood that this invention is not limited to the particular component parts of the compounds described or process steps of the methods described as such compounds and methods may vary. It is also to be understood that the terminology used herein is for purposes of describing particular embodiments only, and is not intended to be limiting. It must be noted that, as used in the specification and the appended claims, the singular forms "a," "an", and "the" include singular and/or plural referents unless the context clearly dictates otherwise. It is moreover to be understood that, in case parameter ranges are given which are delimited by numeric values, the ranges are deemed to include these limitation values. It is moreover to be understood that, in case upper and lower limits of such parameter ranges are given, such limits may be used individually or in combination.

According to one aspect of the invention, a synthetic compound is provided, which compound comprises at least one effector moiety and at least one binder moiety. The effector moiety is connected to the binder moiety, and comprises an N-formyl methionine peptide which comprises an isoleucine residue.

Said N-formyl methionine peptide comprises an N-formyl methionine residue which is located, preferably, N-terminally in said peptide.

The inventors have surprisingly found that synthetic compounds having the specified effector moiety have significant advantages over those having other effector moieties, like fMLF (N-formyl Met-Leu-Phe), fMMYALF (N-formyl-Met-Met-Tyr-Ala-Leu-Phe; SEQ ID NO: 8)), or fML (N-formyl-Met-Leu).

These advantages result in an enhanced efficacy of the effector moieties, and, as such, of a synthetic compound comprising such effector moiety, compared to prior art molecules devoid of such isoleucine residue.

Preferably, the effector moiety is connected to the binder moiety either
  directly, and/or
  via a linker.

Such direct connection can for example be accomplished by means of a direct conjugation, e.g., by means of a covalent bond. A suitable cross-linking agent can be used therefore, e.g., a carbodiimide, like EDC or DCC.

A process for conjugating an N-formyl methionine peptide to a monoclonal antibody by means of a carbodiimide is for example disclosed in Obrist et al, 1988.

A linker, in contrast, consists of a molecule or an oligo- or polymer that binds, at its two respective ends, the effector moiety, and the binder moiety, respectively. Preferred embodiments are discussed further down in this specification.

Preferably, the N-formyl methionine peptide further comprises at least one residue selected from the group consisting of: leucine, phenylalanine, valine, and/or threonine.

Preferably, the compound according to the invention comprises
  (i) an effector moiety located at the base of a Y-shaped structure;
  (ii) optionally, one or two linkers are attached to the effector moiety, and
  (iii) two binder moieties are attached to the other ends of the one or two linkers to form a Y-shaped structure.

Likewise preferable, only one linker is attached to the effector moiety, so that the compound has an I-shape with only one effector moiety and one binder moiety.

Likewise preferable, three or more linkers are attached to the effector moiety, so that the compound has a shape similar to a bunch of flowers, with one effector moiety and three or more binder moieties.

Likewise preferable, two or more linkers are attached to two or more effector moieties, the linkers each carrying a binder on their other end, the linkers further being connected or attached to one another more or less halfway, so that the compound has a shape similar to an X (in case of two linkers connected halfway), or similar to a star (in case of three or more linkers connected halfway).

Likewise preferable, one or more linkers are attached to one or more effector moieties, the linkers being branched more or less halfway into two or more arms, so that each linker carries two or more binders on its other end, so that the compound has, for example, a shape similar to a Y (in case of one linker being branched halfway into two arms).

Depending on the choice of the effectors and binder moieties, the compound can thus be bifunctional (one effector moiety function and one or more binder moieties with the same specificity), or tri- or multifunctional (one effector moiety function and two or more binder moieties with different specificity).

According to a preferred embodiment of the synthetic compound, the effector moiety is a peptide or peptidomimetic.

The term "peptide", as used herein, refers to synthetic or naturally occurring short chains of amino acid monomers linked by peptide (amide) bonds. The shortest peptides are dipeptides, consisting of 2 amino acids joined by a single peptide bond, followed by tripeptides, tetrapeptides, etc. A polypeptide is a long, continuous, and unbranched peptide chain. Peptides are distinguished from proteins on the basis of size, and as an arbitrary benchmark can be understood to contain approximately 70 or less amino acids.

The term "peptidomimetic", as used herein, refers to a compound in which chemical structures (e.g., naturally occurring amino acid residues) of a peptide have been replaced with other chemical structures which mimic the conformation the replaced structures. Examples of peptidomimetics include peptidic compounds in which the peptide backbone is substituted with one or more benzodiazepine molecules (see e. g., James et al. (1993) and "retro-inverso" peptides (see U.S. Pat. No. 4,522,752 to Sisto). The term "peptidomimetic" also refers to a molecule comprising non-naturally occurring amino acids (e.g., a D-amino acid or a modified amino acid) that conformational and functionally serve as a substitute for a particular amino acid in a peptide-containing compound without adversely interfering to a significant extent with the function of the peptide, e.g., FPRL-1 agonists (N-formyl methionine peptide receptor-like-1 agonists).

In a preferred embodiment, the N-formyl methionine peptide is ≤12 amino acids in length, more preferably ≤10 amino acids in length, even more preferably ≤8 amino acids in length.

In another preferred embodiment, the N-formyl methionine peptide is ≥2 amino acids in length, more preferably ≥3 amino acids in length, even more preferably ≥4 amino acids in length. In another preferred embodiment, the effector moiety comprises a peptide of ≤12 and ≥2 amino acids in length, more preferably ≤10 and ≥3 amino acids in length, even more preferably ≤8 and ≥4 amino acids in length.

In another preferred embodiment, the N-formyl methionine peptide comprises, in addition to the at least one isoleucine residue, at least one residue selected from the group consisting of leucine, phenylalanine, valine and/or threonine.

Preferably, the N-formyl methionine peptide comprises, in addition to the at least one isoleucine residue,
  at least one phenylalanine residue and at least one leucin residue, or
  at least one phenylalanine residue, at least one leucin residue and at least one selected from a threonine residue and/or a valine residue.

According to a particularly preferred embodiment, the N-formyl methionine residue is followed, in direction N->C, by
  a first block comprising one or two isoleucine residues, and
  a second block comprising a phenylalanine residue and a leucin in any order relative to one another,
wherein the two blocks can be positioned in any order relative to one another, and are either linked directly or via a peptide sequence comprising up to two amino acid residues.

The term "in direction N->C", as used herein, means that first and second blocks are located C-terminally relative to the N-formyl methionine residue According to a particularly preferred embodiment, the effector moiety comprises, in addition to the N-formyl methionine residue, at least one of the sequence motifs selected from the group consisting of
  IFL
  LFII (SEQ ID NO: 12),
  IVTLF (SEQ ID NO: 13).
  LFIIK (SEQ ID NO: 14), and/or
  IFTLF (SEQ ID NO: 15).

In a preferred embodiment, the N-formyl methionine peptide comprises at least one peptide sequence selected from the group consisting of min, (SEQ ID NO: 3), fMLFII (SEQ ID NO: 4), fMIVTLF (SEQ ID NO: 5), fMLFIIK (SEQ ID NO: 6) and/or fMIFTLF (SEQ ID NO: 7), wherein fM=N-formylmethionine, and wherein the remaining capital letters symbolize L-amino acids under the one letter code.

It is important to mention that amino acid sequences or peptide sequences discussed herein are always shown, herein, in N->C direction.

N-formyl methionine peptides are capable of binding to N-formyl methionine peptide receptors (FPR), which belong to a class of G protein-coupled receptors involved in chemotaxis. These receptors were originally identified by their ability to bind N-formyl methionine peptides such as N-formyl methionine produced by the degradation of either bacterial or host cells. Hence N-formyl methionine peptide receptors are involved in mediating immune cell response to infection. These receptors may also act to suppress the immune system under certain conditions.

N-formyl methionine peptide receptors belong to the superfamily of Pattern recognition receptors (PRRs) which are a primitive part of the immune system. They are proteins expressed by cells of the innate immune system to identify pathogen-associated molecular patterns (PAMPs), which are associated with microbial pathogens or cellular stress, as well as damage-associated molecular patterns (DAMPs), which are associated with cell components released during cell damage. They are also called pathogen recognition receptors or primitive pattern recognition receptors because they evolved before other parts of the immune system, particularly before adaptive immunity.

It is, in this context, important to make clear that these effector peptides are (i) synthetic peptides and (ii) can comprise naturally and/or non-naturally occurring amino acids, e.g., D-amino acids or modified amino acids.

Methods to make synthetic peptides are known to the person skilled in the art. Original protocols to provide such oligopeptides have been published and are known to the skilled person (e.g.; O'Donnell et al (1996)).

Numerous improvements and extensions to the protocols have been found giving this method a high degree of flexibility. The improvements include the incorporation of non-natural amino acids (Ishida & Inoue (1999), O'Donnell et al. (1997), Scott et al. (1997) and the production of cyclic peptides (Zhang & Tam (1997), Koppitz et al. (1997); Gobbo et al. (1997), and Tam & Lu (1998)).

According to another preferred embodiment, the binder moiety is at least one selected from the group consisting of
  a peptide or peptidomimetic;
  an antibody, or a fragment or derivative thereof;
  a receptor molecule, or a fragment or derivative thereof;
  an antibody mimetic, or a fragment or derivative thereof;
  an aptamer;

The terms "peptide" and "peptidomimetic" have the same meaning as above; however, in the present context they also have the capability of binding a given moiety with sufficiently high specificity and/or sensitivity.

As used herein, the term "antibody", shall refer to a monoclonal or polyclonal antibody, or a fragment or derivative thereof. Particularly preferred, such antibody is selected from the group consisting of IgG, IgD, IgE, IgA and/or IgM, or a fragment or derivative thereof.

As used herein, the term "fragment" shall refer to fragments of such antibody retaining, in some cases, target binding capacities, e.g.
  a CDR (complementarity determining region)
  a hypervariable region,
  a variable domain (Fv)
  a single chain variable fragment (scFv)
  an IgG heavy chain (consisting of VH, CH1, hinge, CH2 and CH3 regions)
  an IgG light chain (consisting of VL and CL regions), and/or
  a Fab and/or F(ab)2
  a Fab and/or F(ab)2

As used herein, the term "receptor molecule" is used in its widest context. The receptor molecule may be any chemical entity capable of binding to a given target. Receptor molecules include enzymes, lectins, as well as soluble or membrane bound proteins or glycoproteins to a given ligand.

Examples for such membrane bound proteins are the TNFa receptor or the VEGF receptor, fragments of which are used in the so-called Fc fusion products, e.g. in ethanercept (75 kDa extracellular domain of TNF receptor II fused to human IgG1 Fc) or afflibercept (extracellular domains of VEGF receptors I and II fused to human IgG1 Fc).

As used herein, the term "antibody mimetic" relates to target binding proteins which are not related to immunoglobulins. Many of the above mentioned techniques, like phase display, are applicable for these molecules as well. Such antibody mimetics are for example derived from Ankyrin Repeat Proteins, C-Type Lectins, A-domain proteins of *Staphylococcus aureus*, Transferrins, Lipocalins, Fibronectins, Kunitz domain protease inhibitors, Ubiquitin, Cysteine knots or knottins, thioredoxin A, and so forth, and are known to the skilled person in the art from the respective literature.

The term "aptamer", as used herein, relates to nucleic acid species which are capable of binding to molecular targets such as small molecules, proteins, nucleic acids, and even cells, tissues and organisms. Aptamers are useful in biotechnological and therapeutic applications as they offer molecular recognition properties that rival that of the commonly used biomolecule, antibodies. In addition to their discriminate recognition, aptamers offer advantages over antibodies or other target binders as they can be engineered completely in a test tube, are readily produced by chemical synthesis, possess desirable storage properties, and elicit little or no immunogenicity in therapeutic applications. Aptamers can for example be produced through repeated rounds of in vitro selection or equivalently, SELEX (systematic evolution of ligands by exponential enrichment).

While the enabling examples disclosed in the following refer to a synthetic compound in which the effector moiety is connected to a peptide or peptiomimetic binder moiety, the inventive concept is also enabled in for other types of binder moieties, as e.g., disclosed above. Obrist et al. (1983), for example, discloses a concept in which the binder moiety is a full-size IgG monoclonal antibody, while the effector moiety is fMLP, i.e., an N-formyl methionine peptide devoid of an isoleucine residue. The resulting construct is capable of evoking a local enhancement of macrophages. It is thus clear that the concept according to the invention is not only enabled with peptide binders, but also with other binder types, as set forth above.

Such full size IgG antibody has a molecular weight of about 150 Kd, and an accumulated chain length (2× heavy chain+2× light chain) of about 1330 amino acid residues. In contrast thereto, the peptide or peptiomimetic based binder moieties for which enabling examples are disclosed herein have 10 or less amino acid residues, including non-naturally occurring amino acids. They have thus less than 1% of the size of an IgG.

For this reason, the concept of binding a formyl methionine peptide which comprises an isoleucine residue to a binder moiety is not only functional in case the binder moiety is a (very small) peptide or peptiomimetic; it is also functional in case the binder moiety is a (very large) IgG.

Because the size of other types of binding moieties (receptor molecules, or a fragments or derivatives thereof; antibody mimetics, or fragments or derivatives thereof, or aptamers) falls in the size range that is between an 10 AA peptide and a full IgG, the concept of binding a formyl methionine peptide which comprises an isoleucine residue is also functional with these embodiments.

According to another preferred embodiment of the synthetic compound, the binder moiety targets α3 integrin or αvβ6 integrin, or a subdomain or epitope thereof. Expression of α3 Integrin and/or αvβ6 integrin is associated with different types of cancer. The respective non-antibody compounds provide thus a promising approach to treat these diseases.

Preferably, the binder moiety comprises at least one peptide sequence selected from the group consisting of cdGY(3-NO2)GHypNc (SEQ ID NO: 1, see FIG. 15) or RGDLATLRQL (SEQ ID NO: 2, see FIG. 15), wherein c=D-Cysteine; d=D-Aspartate; 3-NO2=Nitrotyrosine; Hyp=4-Hydroxiproline, and wherein the remaining capital letters symbolize L-amino acids under the established "one letter code." SEQ ID NO: 1 binds to α3 integrin, while SEQ ID NO: 2 binds to αvβ6 integrin.

The term "linker" preferably refers to any structures which operably links at least one effector moiety to at least one binder. If the linker binds covalently to the effector and the binder, its minimum length is one covalent bond, e.g. one peptide bond. Other linkers comprise a variety of chemical linking and crosslinking agents including, for example, homo- or heteromultifunctional, oligo- or heterofunctional crosslinking agents. Linking or crosslinking can be achieved by any of a variety of chemistries well known in the art including, for example, activated polyethylene glycols, aldehydes, isocyanates, maleimides and the like.

As used herein, "operably linked" means that under physiological conditions of pH, ionic strength and osmotic potential, the majority of the entities of the effector and the binder are associated with each other and both entities can exhibit their intended function.

Examples for a linker of the present invention comprise, small linker, statistical coupling by homooligofunctional linker, oligo-alcohols, -amines, -carboxylic acids, thiols, defined stochiometry by heterooligofunctional coupling element, polymer (hydrophilic and lipophilic polymer), statistical coupling by homomultifunctional linker, HPMA, polylysine, hydroxyethylcellulose, hydroxyethylstarch, aminodextran, copolymers, branched polymeric scaffolds, branched PEG, dendrimers, especially polylysine dendrimers, defined stochiometry by heterooligofunctional coupling, polypeptides, functionized activated polymers, polyethyleneglycol (PEG) and/or polyurethanes.

The coupling of the units to the polymeric carrier unit, e.g. PEG, is performed using reactions known to the person skilled in the art. E.g. there are number of PEG and HES attachment methods available to those skilled in the art (see for example WO 2004/100997 giving further references, Roberts et al., 2002; U.S. Pat. No. 4,064,118; EP 1 398 322; EP 1 398 327; EP 1 398 328; WO 2004/024761). Dimerization of molecules via PEGylation, disulfide bridges or lysine side chains is described in WO 96/40772; WO 96/40749; WO 01/38342; WO 01/091780; WO 2004/101611; WO 2004/100997; WO 2004/101600; WO 2004/101606, Wrighton et al., 1997; Johnson et al., 1997). The mentioned methods combine monomeric peptides via a linker structure in order to obtain the desired dimeric or even multimeric molecules.

According to a particularly another preferred embodiment of the synthetic compound, the linker comprises polyethylene glycol (PEG).

As set forth above, the linkers can be straight, or branched. Branched polyethylene glycol linkers ("multi-arm-PEGs") can be prepared as grafted copolymers or by direct polymerization initiated by an oligovalent starter. Multi-arm-PEGs are commonly prepared with free hydroxyl moieties as chain terminators or subsequently modified to yield a functionalized, activated multi-arm-PEG.

According to another preferred embodiment of the synthetic compound, the linker comprises one or more polyethylene glycol molecules of ≤40 monomers in length, or ≥15 monomers in length, or, preferably, between ≤40 and ≥15 monomers in length.

Preferably, the one or two polyethylene glycol molecules are between ≤35 and ≥20 monomers in length, more preferably between ≤24 and ≥21 monomers in length.

The choice of the suitable functional group to which polyethylene glycol may bind is based on the type of available reactive group on the amino acid residue that will be coupled to the PEG. For proteins, typical reactive amino acids include lysine, cysteine, histidine, arginine, aspartic acid, glutamic acid, serine, threonine, tyrosine.

Preferably, the polyethylene glycol linker is bound to the effector moiety by means of one or more amino acid side chain groups. Preferably, said amino acid side chain group is an amino group. Preferably said amino acid residue which has said side chain is a lysine residue. Preferably said amino acid residue which has said side chain is located C-terminal in said effector moiety. In case two or more likers are being used, two or more amino acid residues which have said side chain are located close to one another, e.g., C-terminal.

Preferably, the effector moieties are covalently attached, e.g., via the epsilon amino groups of a lysine residue, through an amide bond to a terminal carboxy group of the polyethylene glycol linker.

According to another preferred embodiment of the synthetic compound, at least two moieties selected from an effector moiety, a binder moiety and a linker are linked to one another by means of click chemistry.

The term "click chemistry" describes a chemistry tailored to generate substances quickly and reliably by joining small units together. Click chemistry is not a single specific reaction, but is meant to mimic nature, which also generates substances by joining small modular units.

As regards the variability of molecules, many naturally occurring molecules are made from repeating units (Proteins are made from repeating amino acid units, and polysaccharides are made from repeating monosaccharide units). The connections are carbon-hetero atom bonds C—X—C, rather than carbon-carbon bonds. In addition, enzymes ensure that chemical processes can overcome large enthalpy hurdles by a series of reactions each requiring only a small energy step. Mimicking nature in organic synthesis is essential in the discovery of new pharmaceuticals given the large number of possible structures.

The size of the pool of drug candidates has been calculated at $10^{63}$, based on the presumption that a candidate consists of fewer than 30 non-hydrogen atoms, weighs less than 500 daltons, is made up of atoms of hydrogen, carbon, nitrogen, oxygen, phosphorus, sulfur, chlorine and bromine, is stable at room temperature, and does not react with oxygen and water. Click chemistry my speed up new drug discoveries by making each reaction in a multistep synthesis fast, effirricient and predictable.

Several reaction types have been identified that fit into the Click chemistry concept neatly:

- [3+2] cycloadditions, such as the Huisgen 1,3-dipolar cycloaddition (also called Azide-Alkyne Huisgen Cycloaddition)
- thiol-ene click reactions
- Diels-Alder reaction and inverse electron demand Diels-Alder reaction
- [4+1] cycloadditions between isonitriles (isocyanides) and tetrazines
- nucleophilic substitution especially to small strained rings like epoxy and aziridine compounds
- carbonyl-chemistry-like formation of ureas but not reactions of the aldol type due to low thermodynamic driving force.
- addition reactions to carbon-carbon double bonds like dihydroxylation or the alkynes in the thiol-yne reaction.

While all these types of reactions qualify as preferred embodiments, the preferred reaction type is [3+2] cycloadditions, preferably, the Azide-Alkyne Huisgen Cycloaddition. This reaction type is a 1,3-dipolar cycloaddition between an azide and a terminal or internal alkyne to give a 1,2,3-triazole.

According to another aspect of the present invention, a pharmaceutical formulation comprising the synthetic compound is provided, which formulation further comprises physiologically acceptable excipients. These excipients can be, for example, buffers, stabilizers, surfactants, cryoprotectives, preservatives and the like. The skilled person finds suitable teaching, e.g. in Frokjaer & Hovgaard, 2000.

According to still another aspect of the present invention, the use of the synthetic compound, or of the formulation, for the treatment of a human or animal subject is provided.

Preferably, said use relates to the treatment of at least one disease selected from the group consisting of:
- Neoplastic diseases
- Autoimmune diseases
- Neuropathological diseases,
- Metabolic diseases and/or
- Infectious diseases.

The term "neoplastic disease", as used herein, refers to an abnormal state or condition of cells or tissue characterized by rapidly proliferating cell growth or neoplasm.

The term "autoimmune diseases" means a disease resulting from an immune response against a self tissue or tissue component, including both self antibody responses and cell-mediated responses.

The term "neuropathological diseases" encompasses, among others, neurodegenerative diseases, neuroinflammatory diseases or seizure disorders.

The term "metabolic diseases" encompasses, among others, means disorders in which errors of metabolism, imbalances in metabolism, or sub-optimal metabolism occur. The metabolic diseases as used herein also contemplate a disease that can be treated through the modulation of metabolism, although the disease itself may or may not be caused by specific metabolism blockage.

The term "infectious diseases" encompasses, among others, diseases caused by pathogens, like parasites (protozoans and metazoans), bacteria, viruses, funghi and mycoplams.

BRIEF DESCRIPTION OF THE EXAMPLES AND DRAWINGS

Additional details, features, characteristics and advantages of the object of the invention are disclosed in the subclaims, and the following description of the respective figures and examples, which, in an exemplary fashion, show preferred embodiments of the present invention. However, these drawings should by no means be understood as to limit the scope of the invention.

Experiments

1. Conjugation Reactions/Click Chemistry

Protocol for the copper-catalyzed azide-alkyne cycloaddition of an effector-peptide carrying two alkyne groups and binder peptides carrying one azide moiety.

Reaction parameters:
1 eq alkyne
2.5 eq azide
1-6 eq $CuSO_4$ (100-200 mM solution in $ddH_2O$)
8-50 eq sodium ascorbate (500-1500 mM solution in $ddH_2O$)
1.2-6.5 eq TBTA (100 mM solution in anhydrous DMF)

Reaction takes place in DMF containing 15-18% $ddH_2O$, at room temperature, under argon atmosphere, in a 2 ml Eppendorf tube stirred by a stirring bar. Concentration of the alkyne is 2-3 mM.

All solutions are prepared freshly before starting the reaction. $ddH_2O$ is degassed and then flushed with argon before preparing the $CuSO_4$ and sodium ascorbate solution.

The reaction is stirred for 10-60 minutes.

The progress of the reaction is monitored by RP-HPLC and ESI-MS.

Reverse phase purification uses a C18 column and a linear gradient from 5-45% B in 30 minutes and the corresponding products are collected by time or mass. The buffers used are A ($ddH_2O$+0.05% TFA) and B (ACN+0.05 TFA). The purified products are lyophilized and stored at −20° C.

2. DHR 123 Oxidation Assay

Oxidative burst in neutrophils form part of the cells host defense, and can be evoked, e.g., by the N-formyl peptide fMLP. (Kim et al, 2003). Oxidation assays are thus a useful tool to determine the potency of formyl peptides. The oxidative burst activity of neutrophils caused by incubation with effector peptides or peptidomimetics was measured by flow cytometry, quantifying the intracellular conversion of dihydrorhodamine 123 (DHR) to rhodamine. In brief, human or murine leukocytes ($1.25*10^6$ cells/ml) were incubated with catalase, cytochalasin B (Sigma) and DHR (Invitrogen) in Hanks' Buffered Saline Solution (HBSS, without $Ca^{2+}$, $Mg^{2+}$) with 10 mM Hepes pH 7.4, 5 mM EDTA and 0.3% BSA at 37° C. for 10 minutes followed by incubation with the different effector peptides or peptidomimetics at different concentrations for 15 minutes at 37° C. PMA was used as a positive control.

All samples were fixed in formaldehyde and kept on ice until analysis using FACS Canto (at least 20,000 cells per sample were counted). Neutrophils were identified based on forward and side scatter characteristics. Analysis of DHR fluorescence was performed by side scatter/FL2 dot plots. Percent of DHR-positive cells were identified by gating on a negative (unstimulated) control sample.

Results are shown in FIGS. 4b, 5, 6c, 7 and 11.

3. FACS Analysis of Cell Binding Assay

The binding capability of peptides or peptidomimectis, of synthetic compounds according to the invention to different cell lines displaying particular targets was investigated by using flow cytometry. Detached cells were incubated with biotinylated peptide/peptidomimetic or biotinylated synthetic compound in blocking buffer for at least 30 min of ice. The cells were washed twice with washing buffer followed by incubation with streptavidin labeled with the Peridininchlorophyll protein PerCP-Cy5.5 (BD Biosciences) for 15 minutes on ice. After one additional wash step, samples were analyzed using FACS Canto (at least 10,000 cells per sample were counted) for cells which have bound the biotinylated reagent plus the streptavidin-PerCP-Cy5.5. Overlay histograms of cells incubated with peptide or control peptide were generated and the geometrical mean fluorescence of each sample was determined in FloJo. The EC50 measurements were calculated using Graph Prism software.

The following cell lines were used. The presence or absence of the surface antigens α3 Integrin and αvβ6 Integrin has been verified by corresponding antibody tests:

| cell line | origin | α3 Integrin | $α_vβ6$ Integrin |
|---|---|---|---|
| A431 | epidermoid carcinoma | + | + |
| PC3 | human prostate cancer cell lines | + | − |
| K 562 | human myelogenous leukemia | − | n/a |
| U87-MG | human primary glioblastoma | + | − |
| HT-29 | human colorectal adenocarcinoma | n/a | + |

4. Chemotaxis Assay

To test for the chemotactic effect of effector peptides or peptidomimetics, human leukocytes were re-suspended in Hanks' Buffered Saline Solution (HBSS, without $Ca^{2+}$, $Mg^{2+}$) with 10 mM Hepes pH 7.4 and 0.3% BSA at $10*10^6$ cells/ml. Cells were pre-warmed at 37° C. for 20 min. After adding the effector dilutions in the above buffer into wells of 24-well plates (800 µl/well), a Millicell culture plate insert with 5 µm pore size was placed in each well, followed by immediate addition of 200 µl (2 million) leukocytes. The plate was incubated at 37° C. for 45 min. The total number of leukocytes that migrated to the bottom chamber was determined using a Neubauer chamber, or the numbers of transmigrated monocytes, neutrophils and lymphocytes were determined by flow cytometry (distinguish cell populations in FCS/SSC plot).

Results are shown in FIGS. 4a, 6a and 6b.

5. Assays to Determine the Potency of Isoleucine Comprising Effector Peptides

In a further Assay, the potency of different isoleucine comprising N-formyl methionine peptides to stimulate respiratory bursts in leukocytes was tested.

Activation of the respiratory, or oxidative, burst was measured by determining NADPH oxidase activity after exposure to the different formyl methionine peptides, some of which comprise isoleucine. The activation of respiratory, or oxidative, bursts is a measure for an immunostimulatory effect on a given molecule on leukocytes.

Isolation of Human Leukocytes

Leukocytes were isolated from heparinized blood from healthy volunteers. Erythrocytes were sedimented by adding dextran 500,000 up to 1% and incubation at 37° C. for 30 minutes. The upper layer containing the leukocytes was subjected to two rounds of hypotonic lysis to eliminate residual erythrocytes. After centrifugation at RT, cell pellets were resuspended in PBS, 10 volumes of sterile distilled water was added and after 20 seconds of incubation at RT 1 original volume of 10× PBS was added. Cells were pelleted again and this lysis step was repeated until a white pellet was observed.

Isolation of Murine Leukocytes

Femurs were dissected from C57BL/6 (Black 6) mice. Bone marrow was flushed out using PBS and a 26 gauge needle. Red cells were lysed using BD Pharm lyse (Becton Dickinson) buffer according to the manufacturer's instructions.

Oxidative Burst Assay/DHR Oxidation Assay

Activation of the oxidative burst (NADPH oxidase activity) was measured using a cell-based dihydrorhodamine (DHR123, Molecular Probes) oxidation assay. Samples of freshly isolated human or murine leukocytes ($2.5×10^5$ cells/ml per sample, in Hank's balanced salt solution (HBSS)+10 mM Hepes, pH 7.3, 0.3% BSA and 5 mM EDTA) were loaded with DHR123 (0.1 mM), catalase (1 U/ml, Sigma-Aldrich) and cytochalasin B (21 µM, Sigma-Aldrich) and pipetted into Eppendorf tubes. Cells were pre-incubated at 37° C. for 10 min followed by the addition of 0.25 volume of effector peptide dilution (5× the intended concentration) prepared in the same buffer. The following N-formyl methionine effector peptides were tested:

| | |
|---|---|
| fMIFL (SEQ ID NO: 3) | comprises isoleucin |
| fMLFII (SEQ ID NO: 4) | comprises isoleucin |
| fMIVTLF (SEQ ID NO: 5) | comprises isoleucin |
| fMLFIIK (SEQ ID NO: 6) | comprises isoleucin |
| fMLF | control |
| fMMYALF (SEQ ID NO: 8) | control |

The mixtures were incubated for 15 min 37° C. Samples were fixed in 1% formaldehyde, put on ice and Hoechst 33258 (0.5 µg/ml) was added to allow for the exclusion of dead cells. Analysis was performed using a FACS Canto (Beckton Dickinson). Gating for live cells and granulocytes was performed in a FCS/Hoechst and a FSC/SSC plot. The percentage of NADPH-oxidase positive granulocytes was identified based on their rhodamine fluorescence in a FL2/SSC plot. An unstimulated sample was used as a reference, a phorbol ester (PMA) stimulated sample was used as a positive control in all assays (not shown). Results are shown in FIGS. 13 and 14

DESCRIPTION OF THE FIGURES

In FIG. 2a, the compound according to the invention resembles the structure of an immunoglobulin G. The effector moiety is located at the base of an Y-shaped structure, similar to the Fc part of an immunoglobulin G; two linkers are attached to the effector moiety, and two identical binder moieties are attached to the other ends of the linkers, in a way similar to the CDRs or the variable domains of immunoglobulin G.

In FIG. 2b, the two linkers carry two different binder moieties, which have, e.g., a specificity for different targets. The compound is thus tri-functional.

In FIG. 2c, one linker is attached to the effector moiety, the linker being branched more or less halfway into two arms, so that each linker carries two binders on its other end, which are different from one another in this example. The compound has, thus a shape similar to an Y.

In FIG. 3a, three linkers are attached to the effector moiety, so that the compound has a shape similar to a bunch of flowers, with one effector moiety and three identical binder moieties.

In FIG. 3b two linkers are attached to two effector moieties, the linkers each carrying a binder on their other end, the linkers further being connected to one another more or less halfway, so that the compound has a shape similar to an X.

Likewise preferred, but not shown in the figures, is that only one linker is attached to the effector moiety, so that the compound has an I-shape with only one effector moiety and one binder moiety.

Further variations are possible. The embodiment in FIG. 2c can, for example, carry two identical binders. The embodiment in FIG. 3a can, for example, carry different binder moieties, which have, e.g., a specificity for different targets.

The embodiment in FIG. 3b can have three or more linkers connected halfway, thus resembling a star. The embodiment in FIG. 3a can have four or more linkers which each carry binder moieties (the same of different ones).

Depending on the choice of the effectors and binder moieties, the compound can thus be bifunctional (one effector moiety function and one or more binder moieties with the same specificity), tri- or multifunctional (one effector moiety function and two or more binder moieties with different specificity), or carry additional functionality (in case a c5 receptor agonist is provided).

The binder moieties can be peptides or peptidomimetics, as well as antibodies, or fragments or derivatives thereof, receptor molecules, or fragments or derivatives thereof, antibody mimetics, or fragments or derivatives thereof, and/or aptamers.

Figure 4:
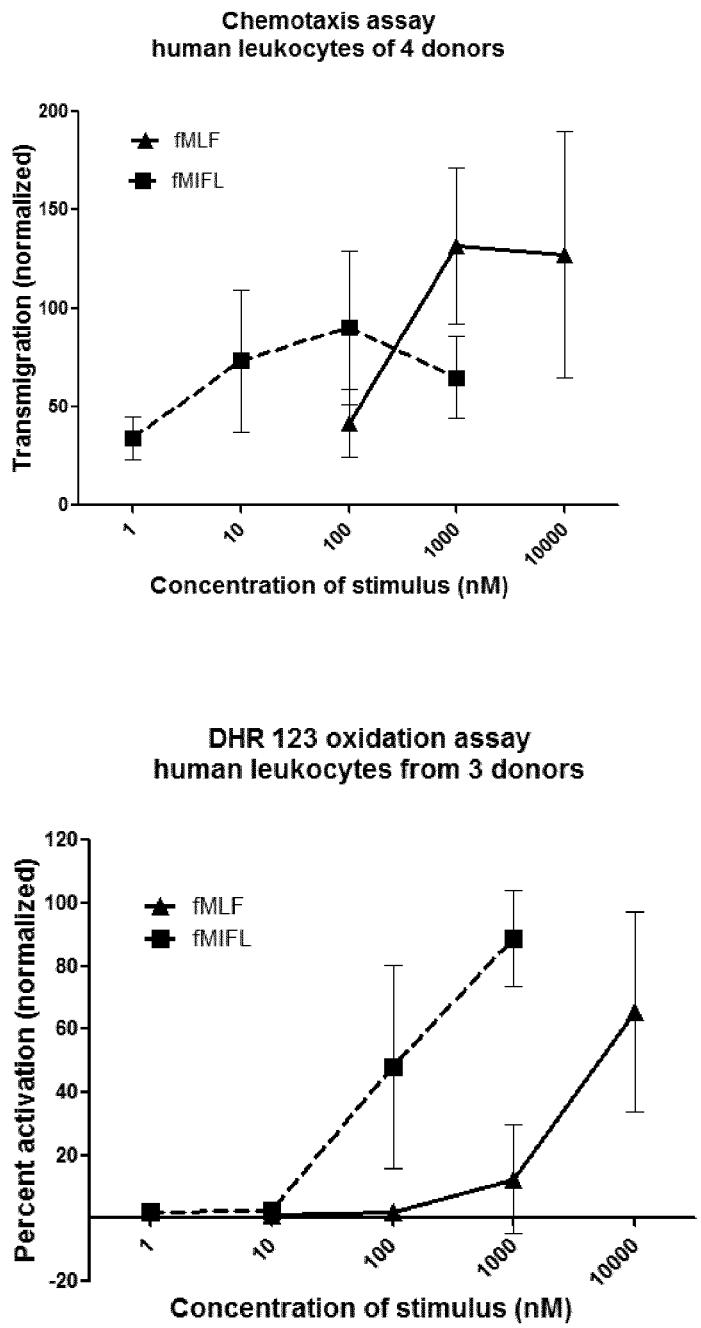

FIG. 4A-B: Chemotaxis assay (A) and DHR 123 oxidation assay (B) comparing fMLF (devoid of an Ile residue) with fMIFL (SEQ ID NO: 3) conjugates in vitro in human leukocytes. fMIFL (SEQ ID NO: 3) demonstrates a significantly better chemotactic effect as well as a much better activation of oxidative bursts.

Figure 5:
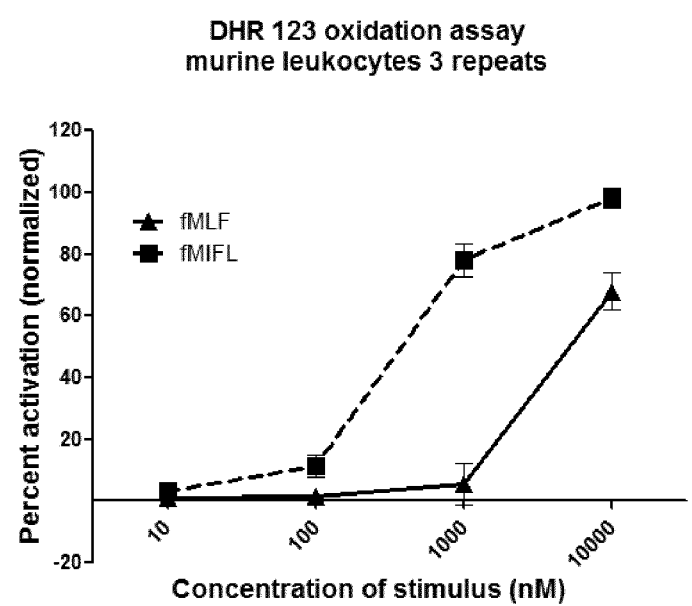

FIG. 5: DHR 123 oxidation assay comparing fMLF (devoid of an Ile residue) with fMIFL(SEQ ID NO: 3) in vitro in mouse leukocytes. fMIFL (SEQ ID NO: 3) demonstrates a much better activation of oxidative bursts.

Figure 6:
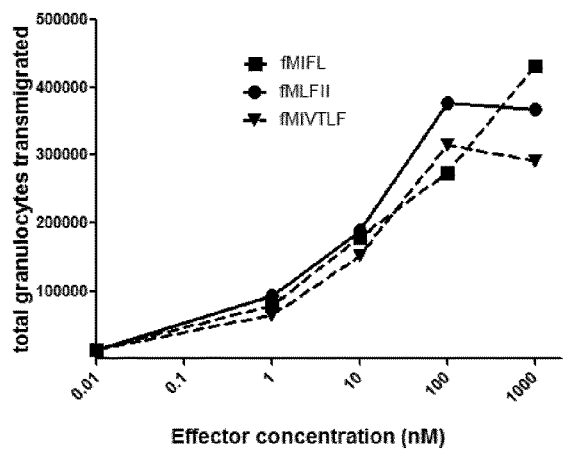
Figure 6:
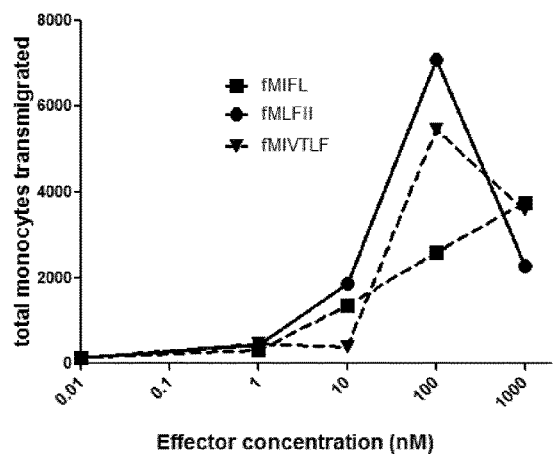
Figure 6:
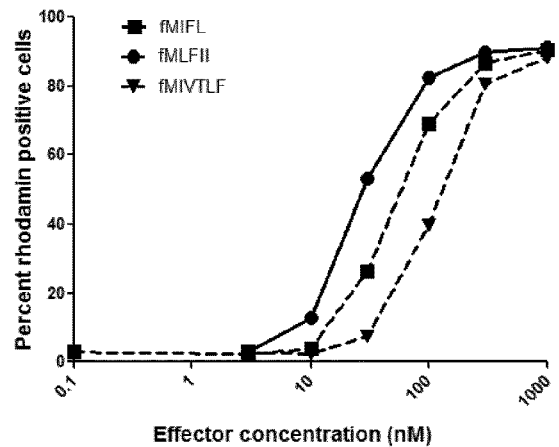

FIGS. 6A-C: Chemotaxis assay with human granulocytes (A), chemotaxis assay with human monocytes (B) and DHR 123 oxidation assay with human leukocytes (C), each assay comparing fMIFL (SEQ ID NO: 3) with fMLFII (SEQ ID NO: 4) and fMIVTLF (SEQ ID NO: 5) in vitro in human leukocytes.

Figure 7:
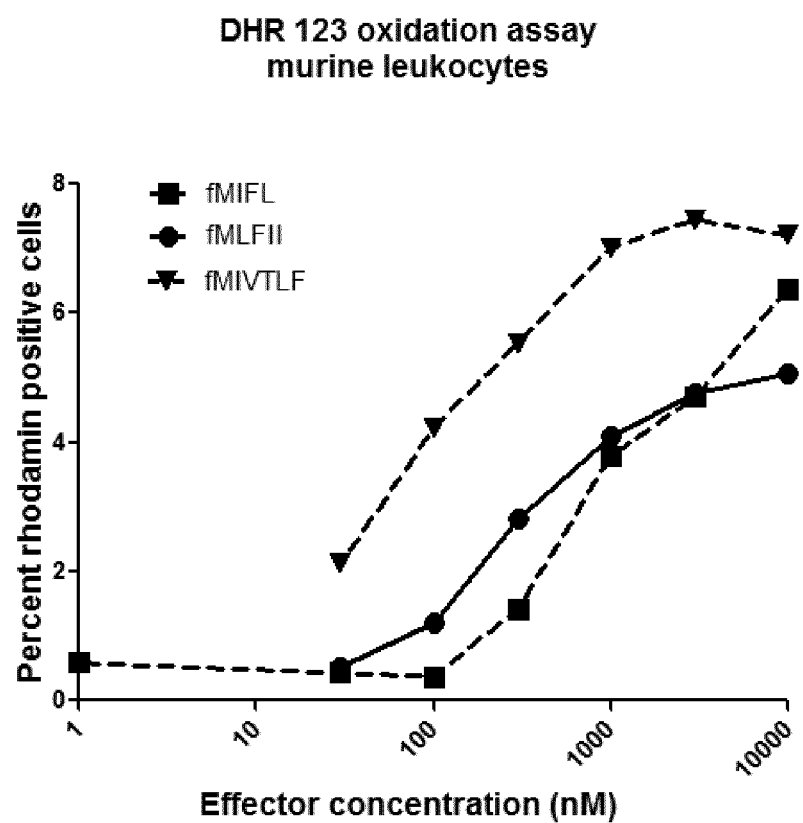

FIG. 7: DHR 123 oxidation assay of assays comparing fMIFL (SEQ ID NO: 3) with fMLFII (SEQ ID NO: 4) and fMIVTLF (SEQ ID NO: 5) in vitro in murine leukocytes.

Figure 8:
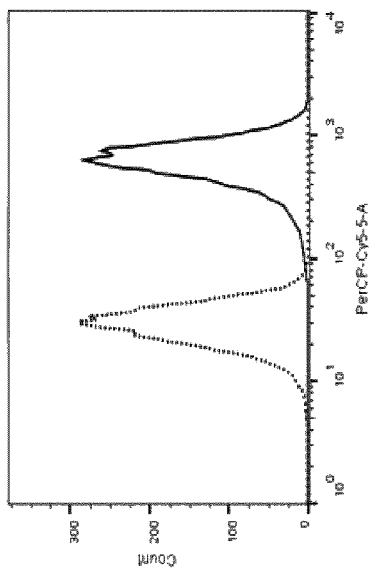
Figure 8:
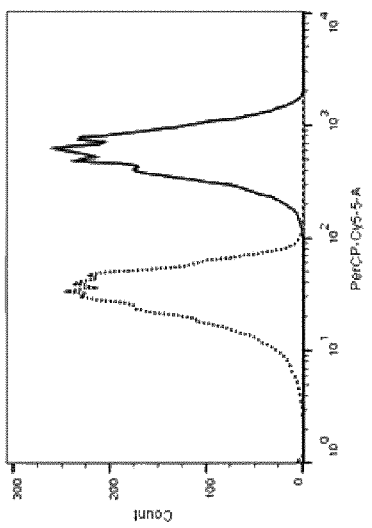
Figure 8:
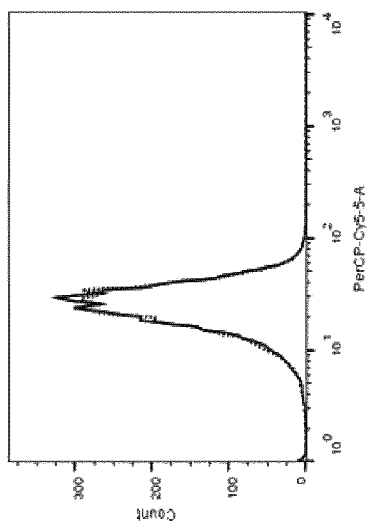
Figure 8:
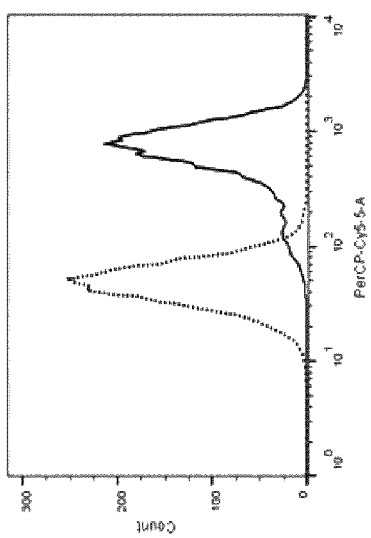

FIG. 8: Human tumor cell lines incubated with 200 nM biotinylated peptidomimetic binder SEQ-ID No 1 targeting α3 Integrin (solid lines), or a scrambled variant of said binder (dotted lines). Staining with Streptavidin-PerCP-Cy5.5. In said scrambled variant, the original peptide's sequence has been permutated randomly.

It can be seen that the binder binds cell lines A431, PC3 and U87-MG, which all express the α3 Integrin surface antigen, while they do not bind the K 562 cell line, which does not express said antigen.

Figure 9:
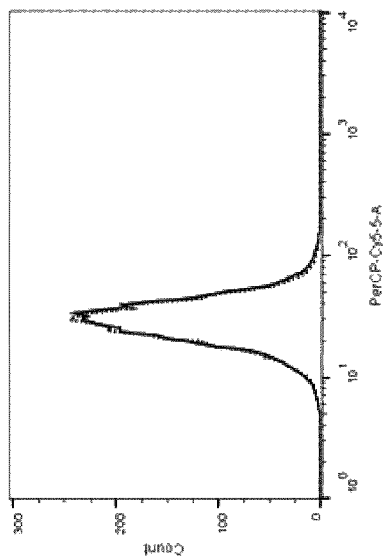
Figure 9:
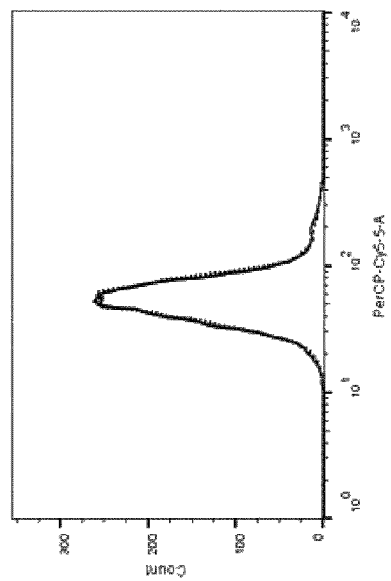
Figure 9:
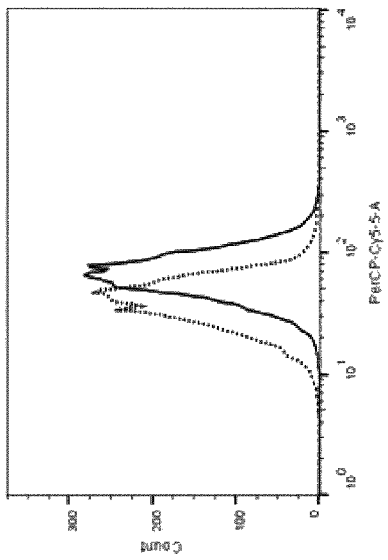
Figure 9:
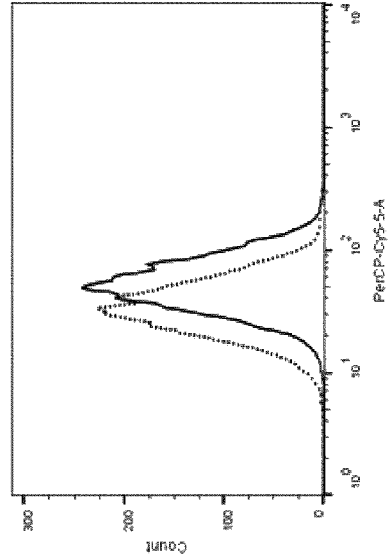

The following cell lines were used. The presence or absence of the surface antigens α3 Integrin and αvβ6 Integrin has been verified by corresponding antibody tests:

FIG. 9: Human tumor cell lines incubated with 10 nM biotinylated peptide binder SEQ ID NO: 2 targeting $α_vβ6$ Integrin (solid lines), or a scrambled variant of said binder (dotted lines). Staining with Streptavidin-PerCP-Cy5.5. In said scrambled variant, the original peptide's sequence has been permutated randomly.

It can be seen that the binder binds cell lines A431, and HT-29, which express the $a_v136$ Integrin surface antigen, while they do not bind cell lines PC-3 and U87-MG which do not express said antigen.

Figure 10:
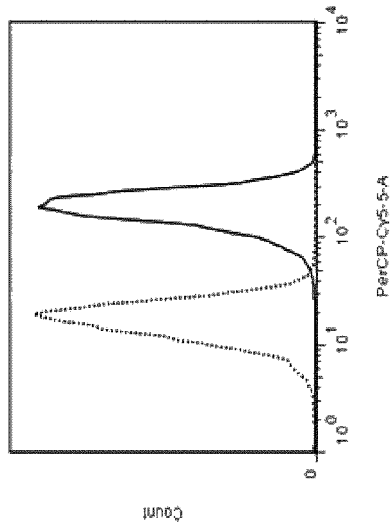
Figure 10:
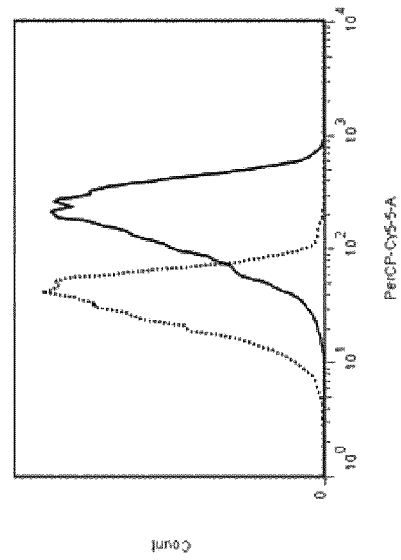
Figure 10:
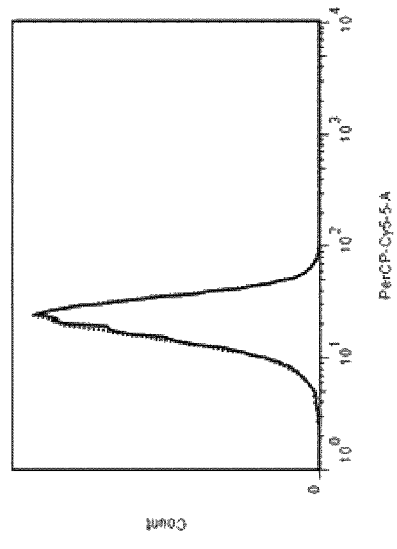
Figure 10:
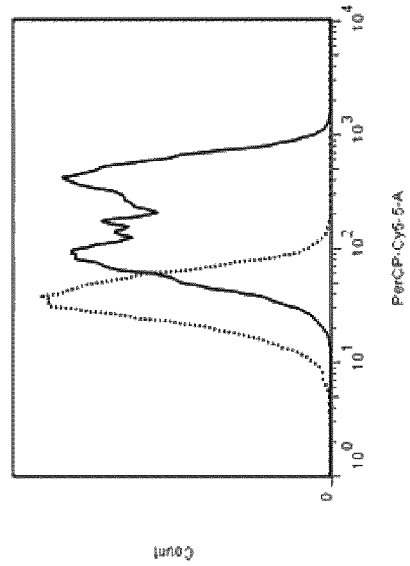

FIG. 10: Human tumor cell lines incubated with 1 μM of synthetic compound type I (solid lines) or no synthetic compound (dotted lines). Stained with Streptavidin-PerCp-Cy5.5. Synthetic compound type I is a synthetic compound consisting of (i) a binder moiety comprising a peptidomimetic having SEQ ID NO: 1, and targeting α3 Integrin, (ii) a PEG linker and an effector moiety comprising a peptidomimetic having SEQ ID NO: 3 (fMIFL). It is obvious that the binding capability of synthetic compound type I to α3 Integrin is similar to that of the mere binder moiety (see FIG. 8). This means that the conjugation of the effector and the linker does not affect the binding capability of the binders.

Figure 11:
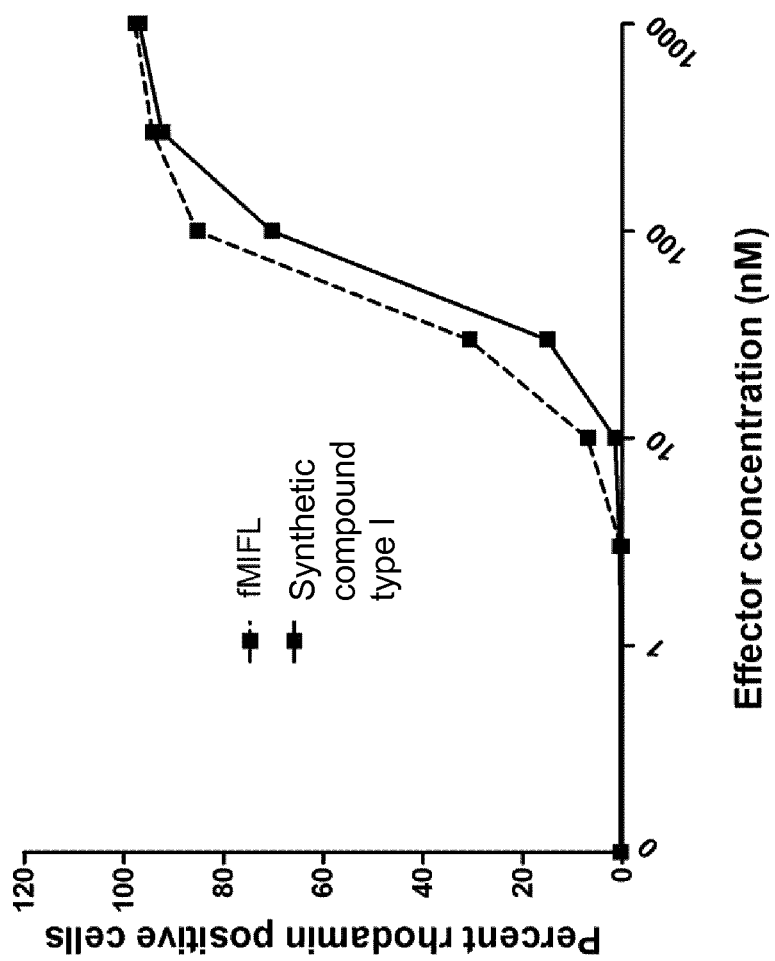

FIG. 11: DHR 123 oxidation assay comparing unconjugated fMIFL (SEQ ID NO: 3) with synthetic compound type I in vitro in mouse leukocytes. Synthetic compound type I is a synthetic compound consisting of (i) a binder moiety comprising a peptidomimetic having SEQ ID NO: 1 and targeting α3 Integrin (see FIG. 15), (ii) a PEG linker and an effector moiety comprising a peptidomimetic having SEQ ID NO: 3 (fMIFL, see FIG. 15). It is obvious that the activation of oxidative bursts of fMIFL (SEQ ID NO: 3) is not affected by conjugation thereof to a PEG-linker and a respective binder peptiodomimetic.

Figure 12:
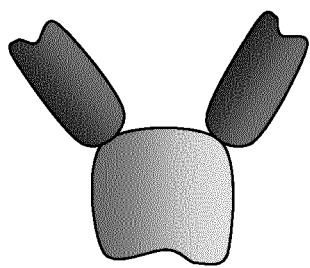

FIG. 12: Another configuration of the synthetic compound according to the invention, which does not have a full-featured linker. Again, the effector moiety is located at the base of an Y-shaped structure, similar to the Fc part of an immunoglobulin G, while two different binder moieties directly connected to the effector moiety, in a way similar to the CDRs or the variable domains of immunoglobulin G.

Such direct connection can for example be accomplished by means of a direct conjugation, e.g., by means of a covalent bond. A suitable cross-linking agent can be used therefore, e.g., a carbodiimide, like EDC or DCC.

The binder moieties can be peptides or peptidomimetiocs, as well as antibodies, or fragments or derivatives thereof, receptor molecules, or fragments or derivatives thereof, antibody mimetics, or fragments or derivatives thereof, and/or aptamers.

Figure 1A:
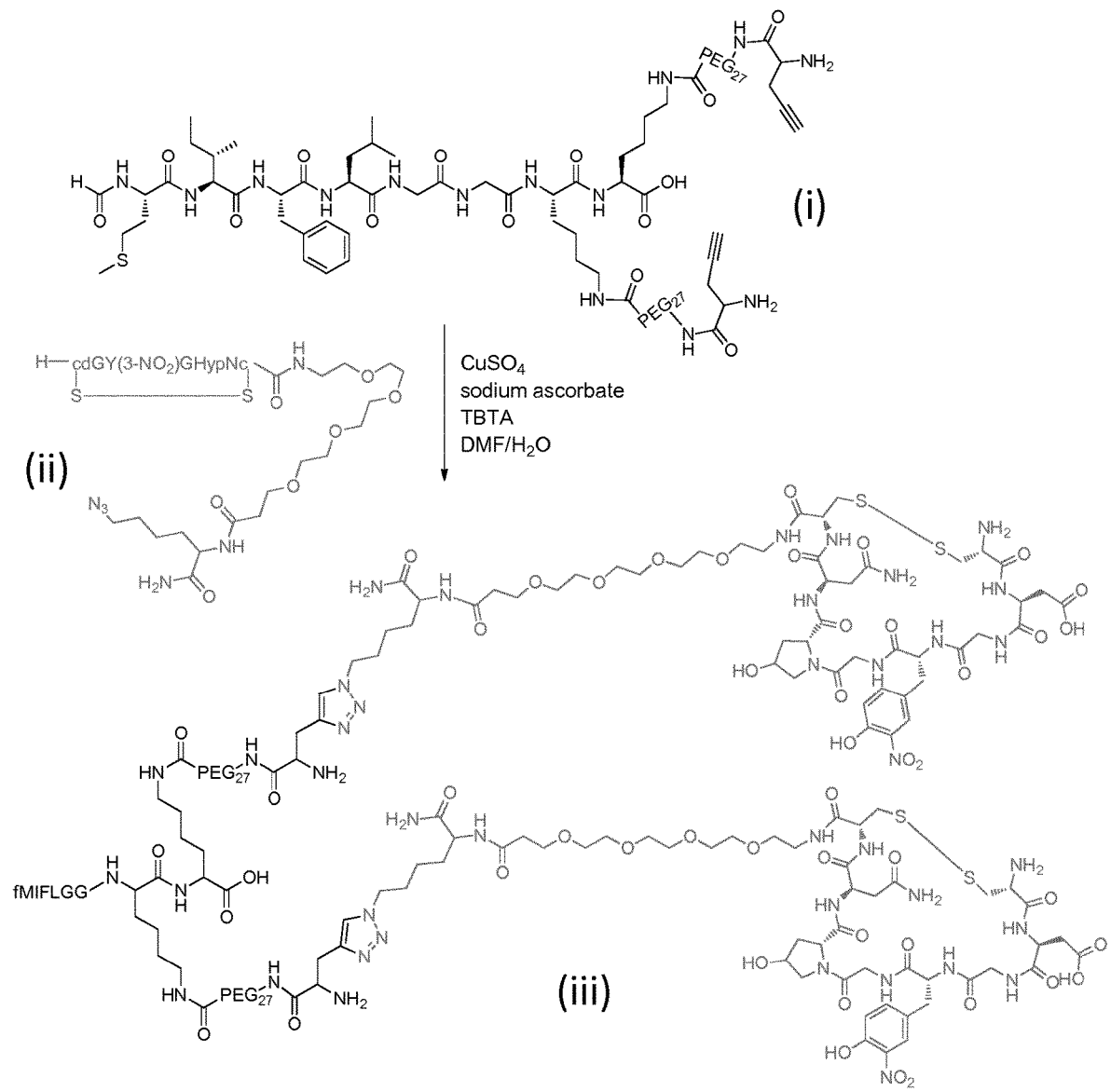
FIG. 1a: Reaction scheme of the Copper-catalyzed [3+2] Azide-Alkyne Cycloaddition. The azide (i) containing the binder peptidomimetic SEQ ID NO: 1 (see FIG. 15) reacts neatly with the alkyne (ii) containing the effector scaffold fMIFL (SEQ ID NO: 3) (see FIG. 15) and the PEG linkers, to afford the 1,4-triazole (iii) at room temperature after only 30 min.
Figure 1B:
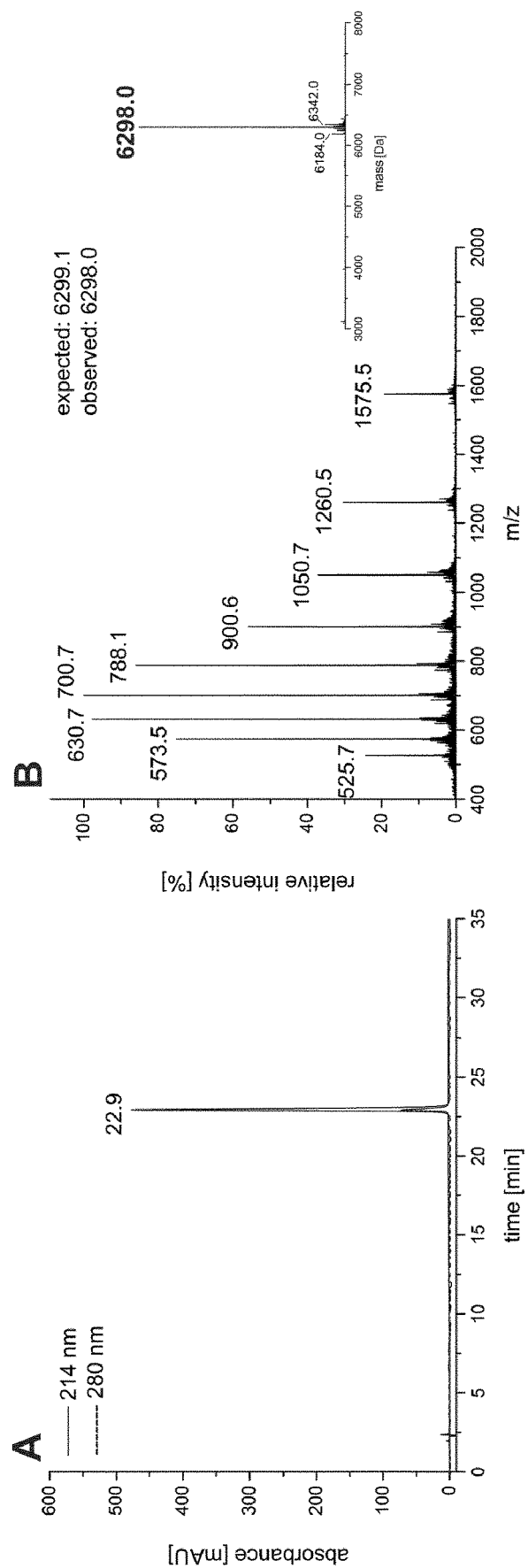
FIG. 1b: Analytical data for the purified compound shown in Scheme 1: A) Reversed phase-HPLC data. B) Electrospray ionization mass spectrometry data of the same compound.
Figure 2:
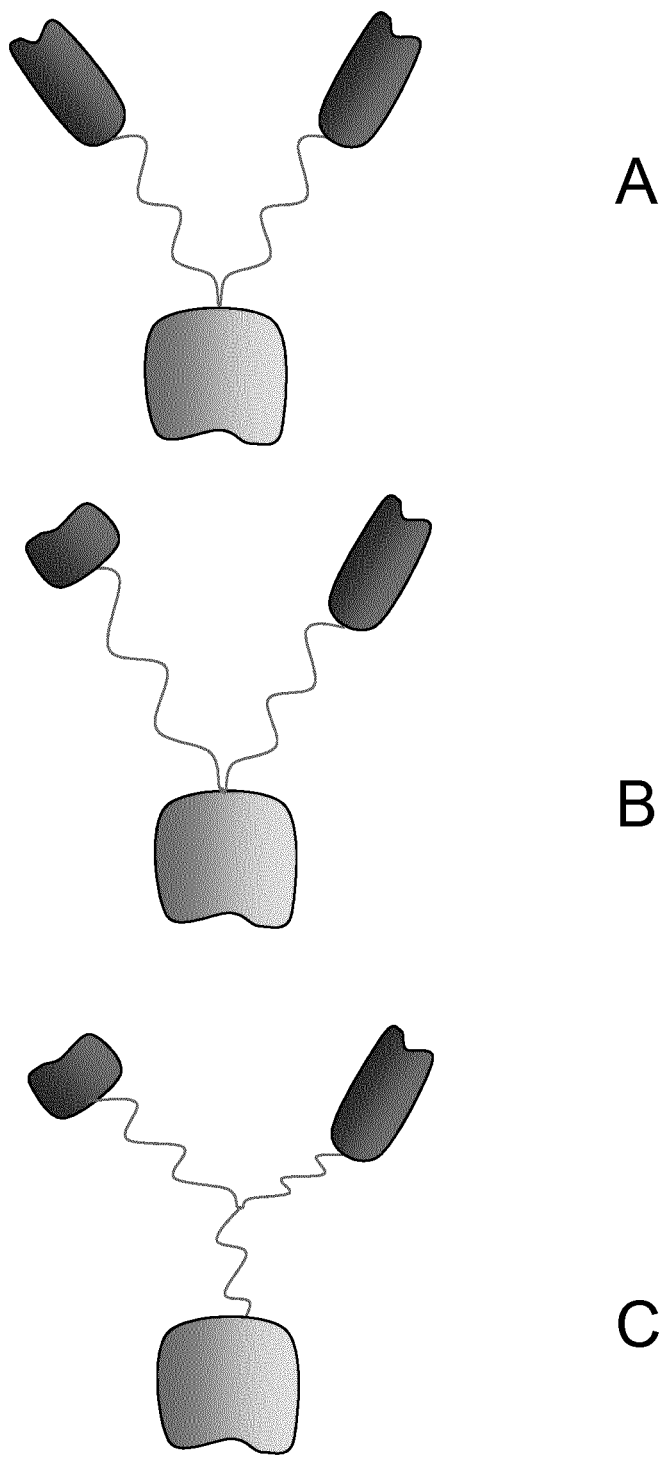
FIGS. 2 and 3 show different configurations of the synthetic compound according to the invention.
Figure 3:
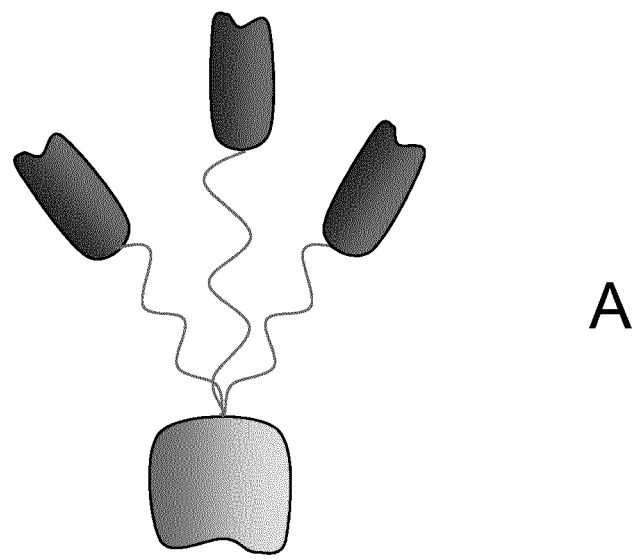
Figure 3:
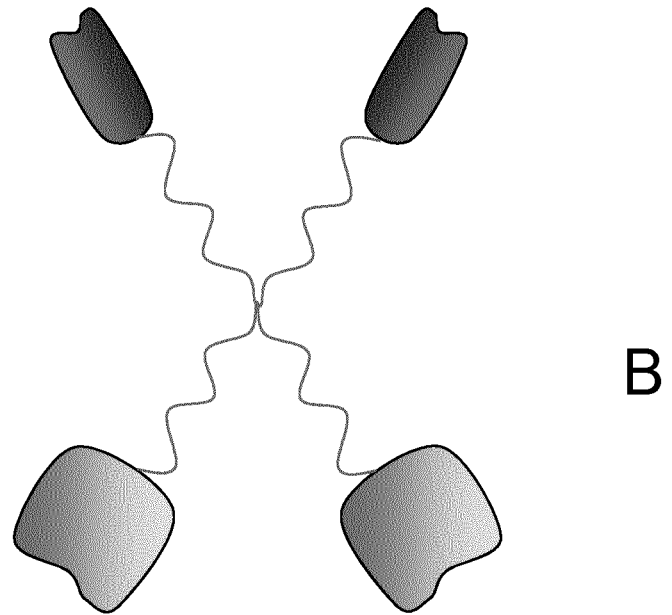

Like set forth in FIGS. 2-3, different variations of this concept are possible, e.g., two identical binder moieties, three or more binder moieties, two or more effector moieties, and so forth.

Figure 13:
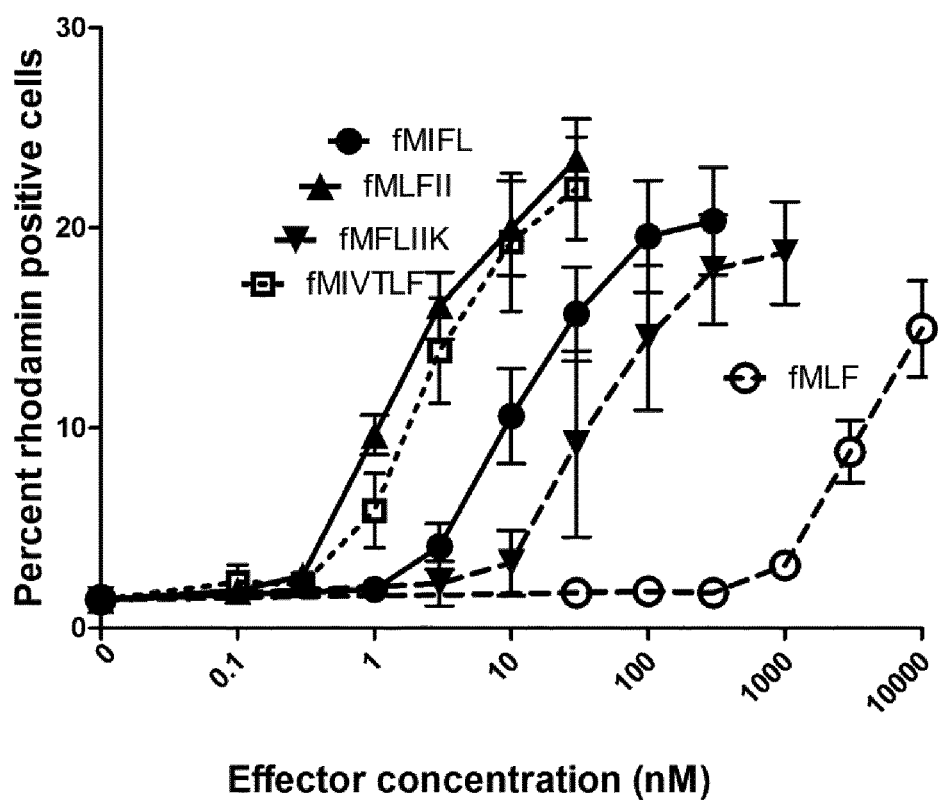

FIG. 13: DHR oxidation assay of murine leukocytes upon exposure to different n-formyl methionine peptides. The share of rhodamine positive cells is a measure for the effector effect of the respective molecule. The four N-formyl methionine effector peptides comprising isoleucine demonstrate a potency which is 2-3 orders of magnitude higher than the control, which does not comprise isoleucine.

Figure 14:
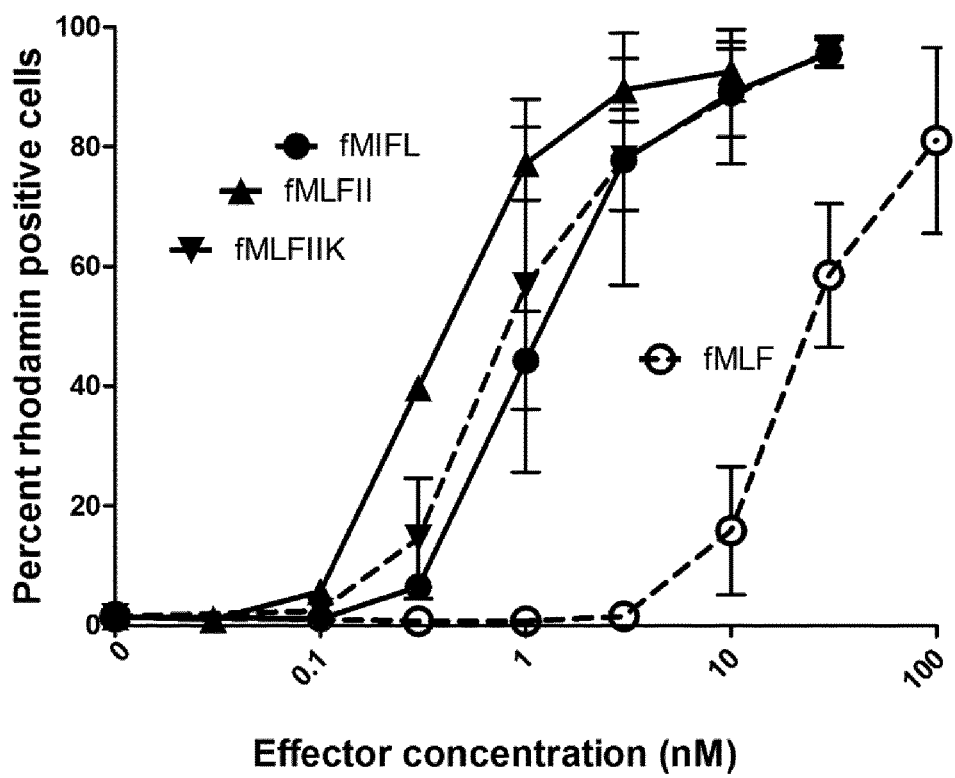

FIG. 14: DHR oxidation assay of human leukocytes upon exposure to different n-formyl methionine peptides. The share of rhodamine positive cells is a measure for the effector effect of the respective molecule. The three N-formyl methionine effector peptides comprising isoleucine demonstrate a potency which is 2-3 orders of magnitude higher than the controls, which do not comprise isoleucine.

FIGS. 13 and 14 demonstrate, impressively, that N-formyl methionine peptides which comprise an isoleucine residue have a much better immuostimulatory effect that N-formyl methionine peptides which lack such isoleucine residue.

FIG. 15: Overview of binder peptides/peptidomimetrics and effector peptides/peptidomimetics discussed herein. It is important to understand N-terminal n-formyl-methionin has the following structure:

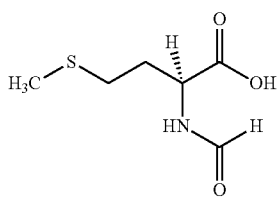

REFERENCES

Frokjaer & Hovgaard, Pharmaceutical Formulation Development of Peptides and Proteins, Taylor & Francis Ltd (2000)

Ishida & Inoue, Reviews on Heteroatom Chemistry, 19, 79-142 (1999)
O'Donnell et al., Tetrahedron Lett., 38, 7163-7166 (1997)
Scott et al., Tetrahedron Lett., 38, 3695-3698 (1997)
Zhang & Tam, J. P., J. Amer. Chem. Soc., 119, 2363-2370 (1997)
Koppitz et al., Helv. Chim. Acta, 80, 1280-1300 (1997)
Gobbo et al., Int. J. Peptide Prot. Res., 50, 336-341 (1997)
Tam & Lu, Protein Sci., 7, 1583-1592 (1998)
James et al. (1993) Science 260: 1937-1942
O'Donnell et al., J. Am. Chem. Soc. 118, 6070 (1996)
Kim et al. J. Immunol. 171:4425-4430 (2003)

Abbreviations
TBTA Tris[(1-benzyl-1H-1,2,3-triazol-4-yl)methyl]amine
DMF N,N-Dimethylformamide
ACN Acetonitrile
HPLC High Performance Liquid Chromatography
ESI-MS Electrospray Ionization Mass Spectrometry
FACS Fluorescence-activated cell sorting
RP-HPLC Reverse-phase High Performance Liquid Chromatography
PEG Polyethylene glycol

What is claimed is:

1. A synthetic compound comprising at least one effector moiety and at least one binder moeity,
   wherein the at least one effector moiety is connected to the binder moiety either directly, and/or via a linker,
   wherein the at least one effector moiety comprises IFL, LFII (SEQ ID NO: 12), IVTLF (SEQ ID NO: 13), LFIIK (SEQ ID NO: 14) or IFTLF (SEQ ID NO: 15), or fMIFL (SEQ ID NO: 3),
   wherein the effector moiety comprises a N-formyl methionine residue,
   wherein the at least one binder moiety consists of a peptide or peptidomimetic, and wherein the peptide or peptidomimetic comprises dCys-dAsp-Gly-NitroTyr-Gly-4HydroxiPro-Asn-dCys or SEQ ID NO: 2.

2. The synthetic compound according to claim 1, in which the N-formyl methionine residue is located N-terminally.

3. The synthetic compound according to claim 1, in which the at least one binder moiety targets α3 integrin or αvβ6 integrin, or a subdomain or epitope thereof.

4. The synthetic compound according to claim 1, in which the linker comprises one or more polyethylene glycol molecules.

5. The synthetic compound according to claim 4 in which the one or more polyethylene glycol molecules is between ≤40 and ≥15 monomers in length.

6. The synthetic compound according to claim 4, in which the polyethylene glycol linker is bound to the effector moiety by means of one or more amino acid side chain groups.

7. The synthetic compound according to claim 1, wherein the at least one effector moiety or one binder moiety are linked to one another by means of click chemistry.

8. A pharmaceutical formulation comprising the synthetic compound according to claim 1, and physiologically acceptable excipients.

9. A method of treating neoplastic diseases, autoimmune diseases, neuropathological diseases, metabolic diseases and/or infectious diseases in a subject, the method comprising administering the synthetic compound of claim 1 to the subject.

10. The synthetic compound according to claim 1, wherein the at least one effector moiety comprises fMIFL (SEQ ID NO: 3), fMLFII (SEQ ID NO: 4), fMIVTLF (SEQ ID NO: 5), fMLFIIK (SEQ ID NO: 6) or fMIFTLF (SEQ ID NO: 7).

* * * * *

```
                         SEQUENCE LISTING

<160> NUMBER OF SEQ ID NOS: 15

<210> SEQ ID NO 1
<211> LENGTH: 8
<212> TYPE: PRT
<213> ORGANISM: Artificial Sequence
<220> FEATURE:
<223> OTHER INFORMATION: SYN-B9; binder to alpha 3 Integrin
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 1

Xaa Xaa Gly Xaa Gly Xaa Asn Xaa
1               5

<210> SEQ ID NO 2
<211> LENGTH: 10
<212> TYPE: PRT
<213> ORGANISM: Artificial Sequence
<220> FEATURE:
<223> OTHER INFORMATION: SYN-B13; binder to alpha v beta 6 Integrin
      (beta chain)

<400> SEQUENCE: 2

Arg Gly Asp Leu Ala Thr Leu Arg Gln Leu
1               5                   10
```

<210> SEQ ID NO 3
<211> LENGTH: 4
<212> TYPE: PRT
<213> ORGANISM: Artificial Sequence
<220> FEATURE:
<223> OTHER INFORMATION: SYN-F2 effector peptide
<220> FEATURE:
<221> NAME/KEY: MISC_FEATURE
<222> LOCATION: (1)..(1)
<223> OTHER INFORMATION: Xaa is formyl methionine

<400> SEQUENCE: 3

Xaa Ile Phe Leu
1

<210> SEQ ID NO 4
<211> LENGTH: 5
<212> TYPE: PRT
<213> ORGANISM: Artificial Sequence
<220> FEATURE:
<223> OTHER INFORMATION: SYN-F4 effector peptide
<220> FEATURE:
<221> NAME/KEY: MISC_FEATURE
<222> LOCATION: (1)..(1)
<223> OTHER INFORMATION: Xaa is formyl methionine

<400> SEQUENCE: 4

Xaa Leu Phe Ile Ile
1               5

<210> SEQ ID NO 5
<211> LENGTH: 6
<212> TYPE: PRT
<213> ORGANISM: Artificial Sequence
<220> FEATURE:
<223> OTHER INFORMATION: SYN-F5 effector peptide
<220> FEATURE:
<221> NAME/KEY: MISC_FEATURE
<222> LOCATION: (1)..(1)
<223> OTHER INFORMATION: Xaa is formyl methionine

<400> SEQUENCE: 5

Xaa Ile Val Thr Leu Phe
1               5

<210> SEQ ID NO 6
<211> LENGTH: 6
<212> TYPE: PRT
<213> ORGANISM: artificial sequence
<220> FEATURE:
<223> OTHER INFORMATION: SYN-F14effector peptide
<220> FEATURE:
<221> NAME/KEY: MISC_FEATURE
<222> LOCATION: (1)..(1)
<223> OTHER INFORMATION: Xaa is formyl methionine

<400> SEQUENCE: 6

Xaa Leu Phe Ile Ile Lys
1               5

<210> SEQ ID NO 7
<211> LENGTH: 6
<212> TYPE: PRT
<213> ORGANISM: artificial sequence
<220> FEATURE:
<223> OTHER INFORMATION: SYN-FXeffector peptide
<220> FEATURE:
<221> NAME/KEY: MISC_FEATURE
<222> LOCATION: (1)..(1)
<220> FEATURE:

```
<221> NAME/KEY: MISC_FEATURE
<222> LOCATION: (1)..(1)
<223> OTHER INFORMATION: Methionine is formyl methionine

<400> SEQUENCE: 7

Xaa Ile Phe Thr Leu Phe
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Methionine is formly methionine

<400> SEQUENCE: 8

Met Met Tyr Ala Leu Phe
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..()
<223> OTHER INFORMATION: Methionine is formyl methionine

<400> SEQUENCE: 9

Met Leu Lys Lys
1

<210> SEQ ID NO 10
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Methionine is formyl methionine

<400> SEQUENCE: 10

Met Leu Pro Lys Lys
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Methionine is formyl methionine

<400> SEQUENCE: 11

Met Leu Phe Lys Lys
1               5

<210> SEQ ID NO 12
```

```
<211> LENGTH: 4
<212> TYPE: PRT
<213> ORGANISM: Artificial Sequence
<220> FEATURE:
<223> OTHER INFORMATION: Synthetic construct

<400> SEQUENCE: 12

Leu Phe Ile Ile
1

<210> SEQ ID NO 13
<211> LENGTH: 5
<212> TYPE: PRT
<213> ORGANISM: Artificial Sequence
<220> FEATURE:
<223> OTHER INFORMATION: Synthetic construct

<400> SEQUENCE: 13

Ile Val Thr Leu Phe
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic construct

<400> SEQUENCE: 14

Leu Phe Ile Ile Lys
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic construct

<400> SEQUENCE: 15

Ile Phe Thr Leu Phe
1               5
```